US00PP27664P3

(12) United States Plant Patent
Marczynski

(10) Patent No.: US PP27,664 P3
(45) Date of Patent: Feb. 14, 2017

(54) ***CLEMATIS* PLANT NAMED 'STEFAN FRANCZAK'**

(50) Latin Name: ***Clematis* hybrid**
Varietal Denomination: STEFAN FRANCZAK

(71) Applicant: Szczepan Marczynski, Pruszkow (PL)

(72) Inventor: Szczepan Marczynski, Pruszkow (PL)

( * ) Notice: Subject to any disclaimer, the term of this patent is extended or adjusted under 35 U.S.C. 154(b) by 116 days.

(21) Appl. No.: 14/544,377

(22) Filed: Dec. 29, 2014

(65) Prior Publication Data

US 2016/0192558 P1 Jun. 30, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

*Primary Examiner* — June Hwu
(74) *Attorney, Agent, or Firm* — Cassandra Bright

(57) ABSTRACT

A new and distinct *Clematis* hybrid named 'STEFAN FRANCZAK' is disclosed, characterized by extremely floriferous plants producing blue-violet, medium size flowers, with undulating margins, and light yellow stamens. Plants bloom over a long period and exhibit compact growth. The new cultivar is a *Clematis* typically suited for ornamental container and landscape use.

1 Drawing Sheet

Latin name of the genus and species: *Clematis* hybrid.
Variety denomination: 'STEFAN FRANCZAK'.

BACKGROUND OF THE INVENTION

The new *Clematis* cultivar is a product of a planned breeding program conducted by the inventor, Szczepan Marczynski, in Pruszkow, Poland. The objective of the breeding program was to produce new compact *Clematis* varieties with novel or new colors. The cross resulting in this new variety was made during 2004.

The seed parent is an unpatented, *Clematis* hybrid proprietary seedling, named '132-99'. The pollen parent is the unpatented, *Clematis* 'Warszawska Nike'. The new variety was identified as a potentially interesting selection in 2006, at a greenhouse in Pruszkow, Poland.

Asexual reproduction of the new cultivar 'STEFAN FRANCZAK' by vegetative tip cuttings was first performed during 2007 , at a greenhouse in Pruszkow, Poland. Subsequent propagation has shown that the unique features of this cultivar are stable and reproduced true to type in 8 successive generations.

SUMMARY OF THE INVENTION

The cultivar 'STEFAN FRANCZAK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'STEFAN FRANCZAK'. These characteristics in combination distinguish 'STEFAN FRANCZAK' as a new and distinct *Clematis* cultivar:

1. Extremely floriferous plants.
2. Blue-Violet medium size flowers, with irregular, streaks and blotches of lighter blue-violet, undulating margins and light yellow stamens.
3. Free flowering habit.
4. Compact plant growth, reaching 1.7 to 2 meters tall.
5. Long blooming period.

PARENTAL COMPARISON

Plants of the new cultivar 'STEFAN FRANCZAK' are similar to plants of the seed parent in most horticultural characteristics, however, plants of the new cultivar 'STEFAN FRANCZAK' differ in the following:

1. Medium size, light blue-violet single flowers. The seed parent has large, white semi double flowers.
2. Undulating tepal margins. The seed parent has flat tepal margins.

Plants of the new cultivar 'STEFAN FRANCZAK' are similar to plants of the pollen parent in most horticultural characteristics, however, plants of the new cultivar 'STEFAN FRANCZAK' differ in the following;

1. Blue-violet flowers. The pollen parent has purple-violet flowers.
2. Undulating tepal margins. The pollen parent has flat tepal margins.

COMMERCIAL COMPARISON

Plants of the new cultivar 'STEFAN FRANCZAK' can be compared to the known commercial variety *Clematis* hybrid 'Rhapsody', unpatented. The *Clematis* varieties have similar flower color and produce similar amounts of tepals. 'STEFAN FRANCZAK' differs from 'Rhapsody' in the following:

1. Different shade of Blue-violet flowers. The comparator has darker and more purple toned flowers.
2. Undulating tepal margins. The comparator has flat tepal margins.

3. Light blue to white colored lines down the tepal center. The comparator has a solid colored tepal.

Plants of the new cultivar 'STEFAN FRANCZAK' can be compared to the known commercial variety *Clematis* 'Sweet Summer Love' U.S. Plant Pat. No. 24,044. The *Clematis* varieties have similar flower color and produce similar amounts of tepals. 'STEFAN FRANCZAK' differs from the comparator in the following:

1. Six to eight tepals. The comparator has 4 tepals
2. Larger flower size.
3. Tepals edges curved inward. The comparator tepal edges curved slightly outward.

BRIEF DESCRIPTION OF THE PHOTOGRAPH

The accompanying photograph in FIG. 1 illustrates in full color typical flowers and foliage of 'STEFAN FRANCZAK' grown outdoors in Pruszkow, Poland. This plant is approximately 3 years old, grown outdoors. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995, except where general terms of ordinary dictionary significance are used. The following observations and measurements describe 'STEFAN FRANCZAK' plants grown outdoors in Pruszkow, Poland. The growing temperature ranged from approximately 15° C. to 18° C. at night to 18° C. to 27° C. during the day. No artificial light, photoperiodic treatments or chemical treatments were given to the plants. Measurements and numerical values represent averages of typical flowering types.

Botanical classification: *Clematis* hybrid 'STEFAN FRANCZAK'.

Age of the plant described: Approximately 3 years old.

PROPAGATION

Typical method: Stem cuttings.

Time to initiate rooting: Approximately 10 days at 18-24° C.

Time to produce a rooted plantlet: 20-30 days at 18-24° C.

Root description: Moderate density, moderate branching, and medium thickness, fleshy in texture.

Root color: Near RHS Grey-orange 165B.

Root diameter: 100-150 cm.

PLANT

Growth habit: Perennial climbing vine.

Height: Approximately 170 to 200 cm.

Plant spread: Approximately 150-200 cm.

Crop time to flower: 1-2 years.

Growth rate: 150-200 cm per year.

Branching characteristics: Opposite facing, basal branching.

Stem length: Approximately 100-150 cm.

Diameter of stem: Approximately 0.2 to 0.4 cm.

Stem color: Young, near RHS Greyed-orange 177A. Mature, near RHS Greyed-orange 175B.

Lateral stem texture: Ribbed.

Number of lateral branches: 4-5.

Number of leaves per lateral branch: 20 to 30.

Internode length: Approximate range 7 cm to 15 cm.

FOLIAGE

Leaf:

*Arrangement*.—Opposite, single and ternate.

*Overall leaf length*.—Average 10-15 cm.

*Overall leaf diameter*.—Average 3-8 cm.

*Shape of blade*.—Elliptic, variable, some entirely elliptic, some 2 and 3 lobed.

*Apex*.—Acute.

*Base*.—Rounded.

*Attachment*.—Stalked.

*Margin*.—Entire and undulating.

*Texture of both surfaces*.—Glabrous.

*Color*.—Young foliage upper side: Near RHS Yellow-green 144A. Young foliage under side: Near RHS Yellow-green 146C. Mature foliage upper side: Near RHS Yellow-green 147A. Mature foliage under side: Near RHS Yellow-green147B.

*Venation*.—Type: Palmate. Venation color upper side: Near RHS Yellow-green 144A. Venation color under side: Near RHS Yellow-green 146C.

Petiole:

*Length*.—Average range 4-10 cm.

*Diameter*.—Approximately 0.1 cm.

*Texture*.—Smooth.

*Color*.—Upper: Near RHS Greyed-purple 183A. Lower: Near RHS Yellow-green 144B.

FLOWER

Bloom period: Natural Season: Summer. Many flowers produced during June through July. During September a second flowering occurs, with less flowers.

Flower type: Single, rotate flower with tepals slightly overlapping. Flowering occurring on both previous year's growth and current year's growth.

Flower aspect: Upward or outward facing, mainly flat.

Rate of flower opening: Approximately 1 -2 days from bud to fully opened flower.

Flower longevity on plant: Approximately 10-14 days, after fully opened. Partly self-cleaning.

Quantity of flowers per lateral stem: 25.

Quantity of flowers per plants: 200 to 300.

Inflorescence size:

*Diameter*.—Average 8 to 10 cm.

*Depth*.—Average 7.0 cm.

Tepal:

*Tepal margin*.—Entire, undulate.

*Tepal tip*.—Sharply acute.

*Tepal base*.—Attenuate.

*Tepal length*.—4 to 5.5 cm.

*Tepal width*.—3 to 4 cm.

Color:

*Tepals*.—When opening: Upper surface: Near RHS Violet-blue 94C with 94A edges. Lower surface: Near RHS Yellow-green 145B with Violet-blue 94A edges.

*Fully opened*.—Upper surface: Near RHS Violet-blue 93D with 89D edges. Center streaks near Violet-Blue 91D Faint basal blotch near White 155D. Lower surface: Near RHS Violet-blue 94D with Yellow-green 150C streaks.

Bud:

*Shape*.—Narrow ovate.

*Length*.—Approximately 3-3.5 cm.

*Diameter*.—Approximately 1.5 cm.

*Color*.—Near RHS Yellow-green 145A and 145D.

Pedicels:

*Length*.—Average range 10 to 18 cm.

*Width*.—Approximately 0.4 cm.

*Angle*.—Average 45° to 80°.

*Strength*.—Flexible.

*Color*.—Near RHS Green 143A.

Fragrance: None.

REPRODUCTIVE ORGANS

Stamens:

*Number*.—Average 30-45 per flower.

*Anther length*.—Approximately 0.4-0.5 cm.

*Anther color*.—Near RHS Yellow 6A.

*Anther shape*.—Oblong.

*Filament length*.—Approximately 1.5 cm.

*Filament color*.—Near RHS Yellow 4D.

*Pollen quantity*.—Much.

*Pollen color*.—Near RHS Yellow 6D.

Pistil:

*Number*.—40-50.

*Length*.—Approximately 1-1.2 cm.

*Style length*.—Approximately 0.5 cm.

*Style color*.—Near RHS Yellow-green 144C.

*Stigma*.—Shape: Rounded. Color: Near RHS Yellow-Green 154C.

*Ovary color*.—Near RHS Yellow-green 144C.

OTHER CHARACTERISTICS

Seeds:

*Quantity of seeds*.—40-50.

*Seed length*.—3 cm.

*Seed diameter*.—0.4 cm.

*Seed color*.—Immature: Near RHS Yellow-green 145A. Mature: Between Near RHS Greyed-orange 164A-166A.

Disease/pest resistance: Neither resistance nor susceptibility to normal diseases and pests of *Clematis* has been observed.

Temperature tolerance: USDA zones 4 through 9.

What is claimed is:

1. A new and distinct cultivar of *Clematis* hybrid plant named 'STEFAN FRANCZAK' as herein illustrated and described.

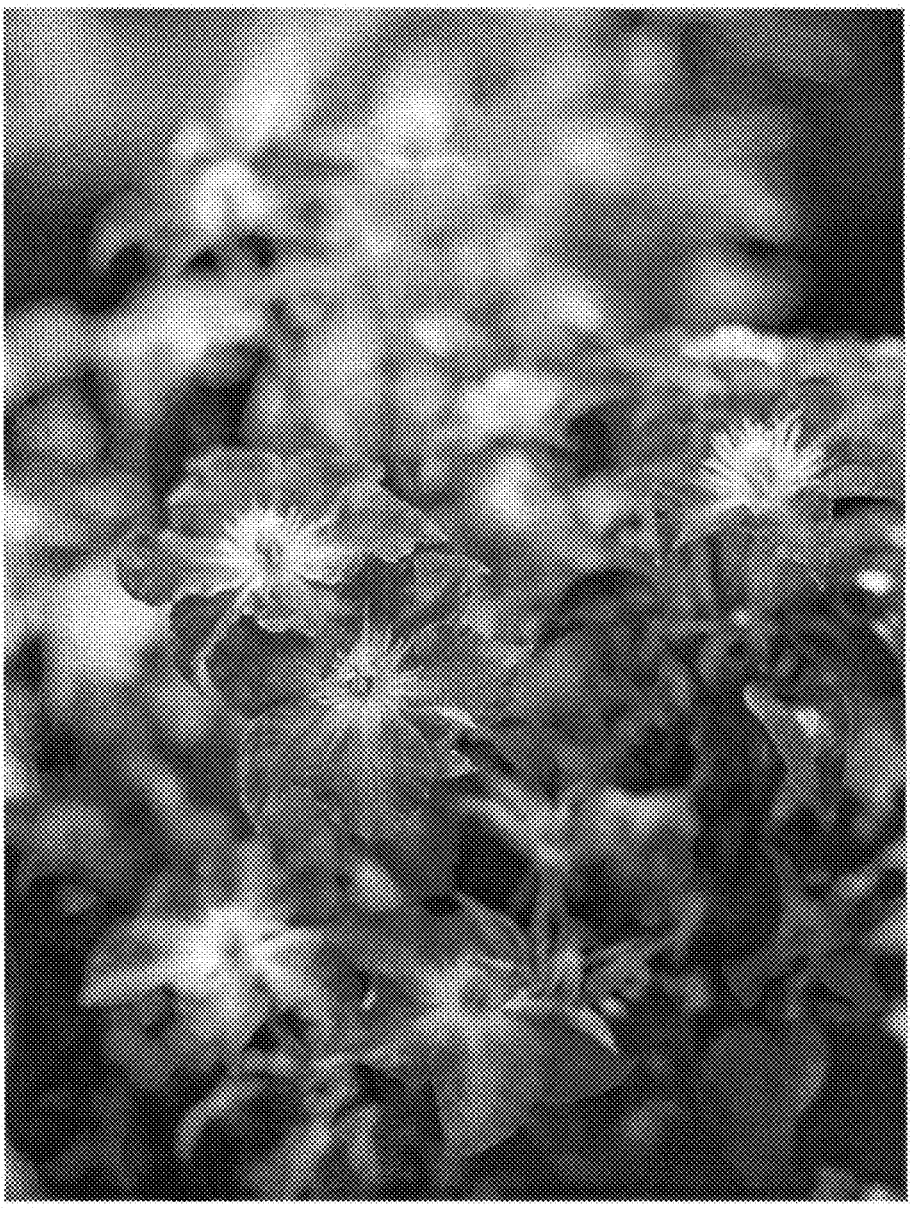

* * * * *